(12) United States Patent
Loy

(10) Patent No.: US 6,409,706 B1
(45) Date of Patent: Jun. 25, 2002

(54) SAFETY SYRINGE, FLUID COLLECTION DEVICE, AND ASSOCIATED METHODS

(76) Inventor: Randall A. Loy, 3093 Timpana Point, Longwood, FL (US) 32779

( * ) Notice: Subject to any disclaimer, the term of this patent is extended or adjusted under 35 U.S.C. 154(b) by 0 days.

(21) Appl. No.: 09/312,440

(22) Filed: May 14, 1999

(51) Int. Cl.⁷ .............................. A61M 5/32; A61M 5/00
(52) U.S. Cl. ....................................... 604/198; 604/110
(58) Field of Search ................................. 604/187, 192, 604/197, 198, 110, 263, 162, 117

(56) References Cited

U.S. PATENT DOCUMENTS

| | | | |
|---|---|---|---|
| 4,735,618 A | * | 4/1988 | Hagen .......................... 604/192 |
| 4,935,013 A | * | 6/1990 | Haber et al. ................. 604/192 |
| 5,026,353 A | | 6/1991 | Bartman |
| 5,059,184 A | | 10/1991 | Dyke |
| 5,061,251 A | | 10/1991 | Juhasz |
| 5,106,379 A | | 4/1992 | Leap |
| 5,135,510 A | | 8/1992 | Maszkiewicz et al. |
| 5,232,456 A | | 8/1993 | Gonzalez |
| 5,242,416 A | | 9/1993 | Hutson |
| 5,250,031 A | * | 10/1993 | Kaplan et al. ............... 604/110 |
| 5,256,152 A | * | 10/1993 | Marks .......................... 604/198 |
| 5,279,579 A | | 1/1994 | D'Amico |
| 5,295,972 A | * | 3/1994 | Mischenko .................. 604/192 |
| 5,304,192 A | * | 4/1994 | Crouse ........................ 604/181 |
| 5,318,538 A | | 6/1994 | Martin |
| 5,527,297 A | | 6/1996 | Paul |
| 5,591,138 A | | 1/1997 | Vaillancourt |
| 5,595,566 A | | 1/1997 | Vallelunga et al. |
| 5,630,803 A | | 5/1997 | Tamaro |
| 5,651,774 A | | 7/1997 | Taranto et al. |
| 5,735,823 A | | 4/1998 | Berger |
| 5,807,352 A | | 9/1998 | Tamaro |
| 5,817,064 A | | 10/1998 | DeMarco et al. |
| 5,817,070 A | | 10/1998 | Tamaro |
| 5,843,041 A | | 12/1998 | Hake et al. |
| 5,843,047 A | | 12/1998 | Pyrozyk et al. |
| 5,853,390 A | | 12/1998 | Freschi |

OTHER PUBLICATIONS

Becton Dickinson, SafetyGlide Needle product brochure, 1/96.

* cited by examiner

Primary Examiner—Michael J. Hayes
(74) Attorney, Agent, or Firm—Allen, Dyer, Doppelt, Milbrath & Gilchrist, P.A.

(57) ABSTRACT

A safety mechanism is for shielding a needle tip, such as for medical implements including syringes and fluid collection devices. The safety mechanism has a sheath that has a longitudinal bore extending from a distal end to a proximal end. The bore is adapted to slidingly admit at least a distal portion of a needle. The safety mechanism further includes a pair of arms, each of which has a proximal end that is affixed adjacent a distal end of a medical implement housing and a distal end that is affixed adjacent the sheath's proximal end. The arms are movable between a shielding position wherein the sheath is in covering relation to a tip of the needle and an injecting position wherein the needle tip extends beyond the sheath's distal end. The arms are biased to the shielding position and are lockable in the shielding position.

7 Claims, 5 Drawing Sheets

US 6,409,706 B1

SAFETY SYRINGE, FLUID COLLECTION DEVICE, AND ASSOCIATED METHODS

BACKGROUND OF THE INVENTION

1. Field of the Invention

The present invention relates to medical devices, and, more particularly, to syringes and fluid collection devices having protective elements for preventing needle accidents.

2. Description of Related Art

Health personnel concern over inadvertent needle sticks has become more acute with the growing awareness of high-profile blood-borne diseases such as AIDS and the various forms of hepatitis. Consequently many designs have been disclosed for minimizing the risk of such exposure.

Among the safety needles known in the art are those described in the patents of Juhasz (U.S. Pat. No. 5,061,251), Maszkiewicz et al. (U.S. Pat. No. 5,135,510), Tamaro (U.S. Pat. Nos. 5,630,803; 5,807,352; 5,810,784; and 5,817,070), Taranto et al. (U.S. Pat. No. 5,651,774), Berger (U.S. Pat. No. 5,735,823), De Marco et al. (U.S. Pat. No. 5,817,064), Hake et al. (U.S. Pat. No. 5,843,041), and Pyrozyk et al. (U.S. Pat. No. 5,843,047).

SUMMARY OF THE INVENTION

It is therefore an object of the present invention to provide a safety syringe.

It is an additional object to provide such a safety syringe that automatically shields the needle tip after usage.

It is a further object to provide such a safety syringe that locks in the shielded position after usage.

It is another object to provide a method of delivering an injection in a manner that prevents inadvertent needle sticks.

It is yet an additional object to provide a method a making a safety syringe.

It is yet a further object to provide a safety blood or other fluid collection device.

It is yet another object to provide a method of collecting blood or other fluid samples in a manner that prevents inadvertent needle sticks.

These objects and others are attained by the present invention, which includes a safety mechanism for shielding a needle tip, such as for medical implements including syringes and fluid collection devices. The safety mechanism comprises a sheath that has a longitudinal bore extending from a distal end to a proximal end. The bore is adapted to slidingly admit at least a distal portion of a needle.

The safety mechanism further includes a pair of arms, each of which has a proximal end that is affixed adjacent a distal end of a medical implement housing and a distal end that is affixed adjacent the sheath's proximal end. The arms are movable between a shielding position wherein the sheath is in covering relation to a tip of the needle and an injecting position wherein the needle tip extends beyond the sheath's distal end.

Means for biasing the arms to the shielding position are provided, as are means for locking the arms in the shielding position.

Also included in the present invention are a syringe and a fluid (e.g., blood) collection device having such a safety mechanism affixed thereto, as well as methods for using and making such devices.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figures 1, 1A:
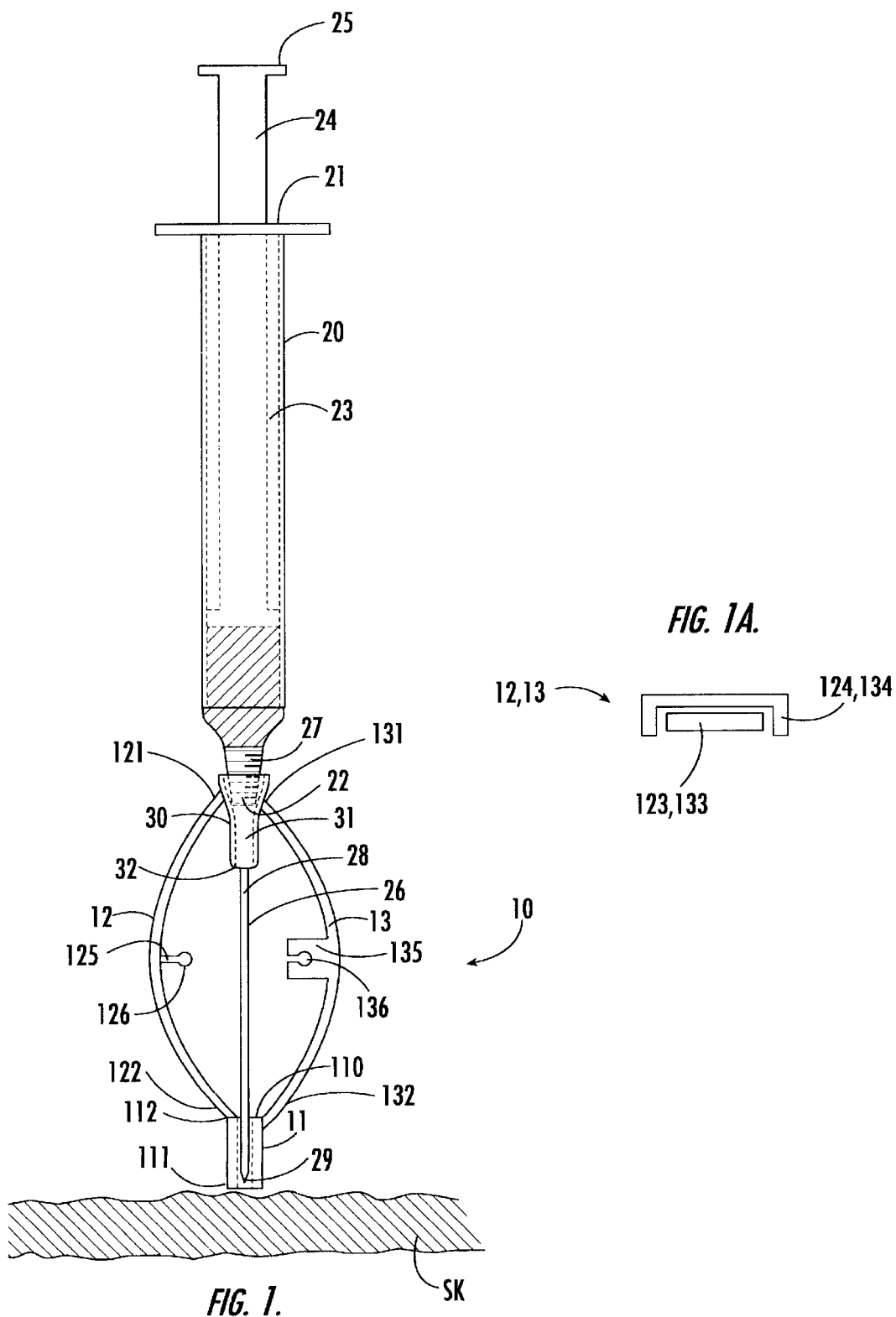
FIG. 1 is a side perspective view of a safety syringe prior to usage in the shielded position.
FIG. 1A is a cross-sectional view of an arm illustrating the housing and metal strip.

A description of the preferred embodiments of the present invention will now be presented with reference to FIGS. 1–5.

A first aspect of the present invention comprises a safety syringe that includes a barrel 20 having a proximal 21 and a distal opening 22 and an interior space 23. A plunger 24 is adapted to slide within the barrel's interior space 23 from the proximal end 25. The barrel 20 has a mating portion at its distal end 27, such as an externally threaded area as is known in the art for receiving a Luer-Lok™-type mating element 30. Such a mating element 30 has a longitudinal bore 31 therethrough.

A needle 26 is affixed to the mating element 30 at its distal end 32. The needle 26 has a bore 28 that is in communication with the barrel's distal opening 22 and a distal tip 29.

Figure 2:
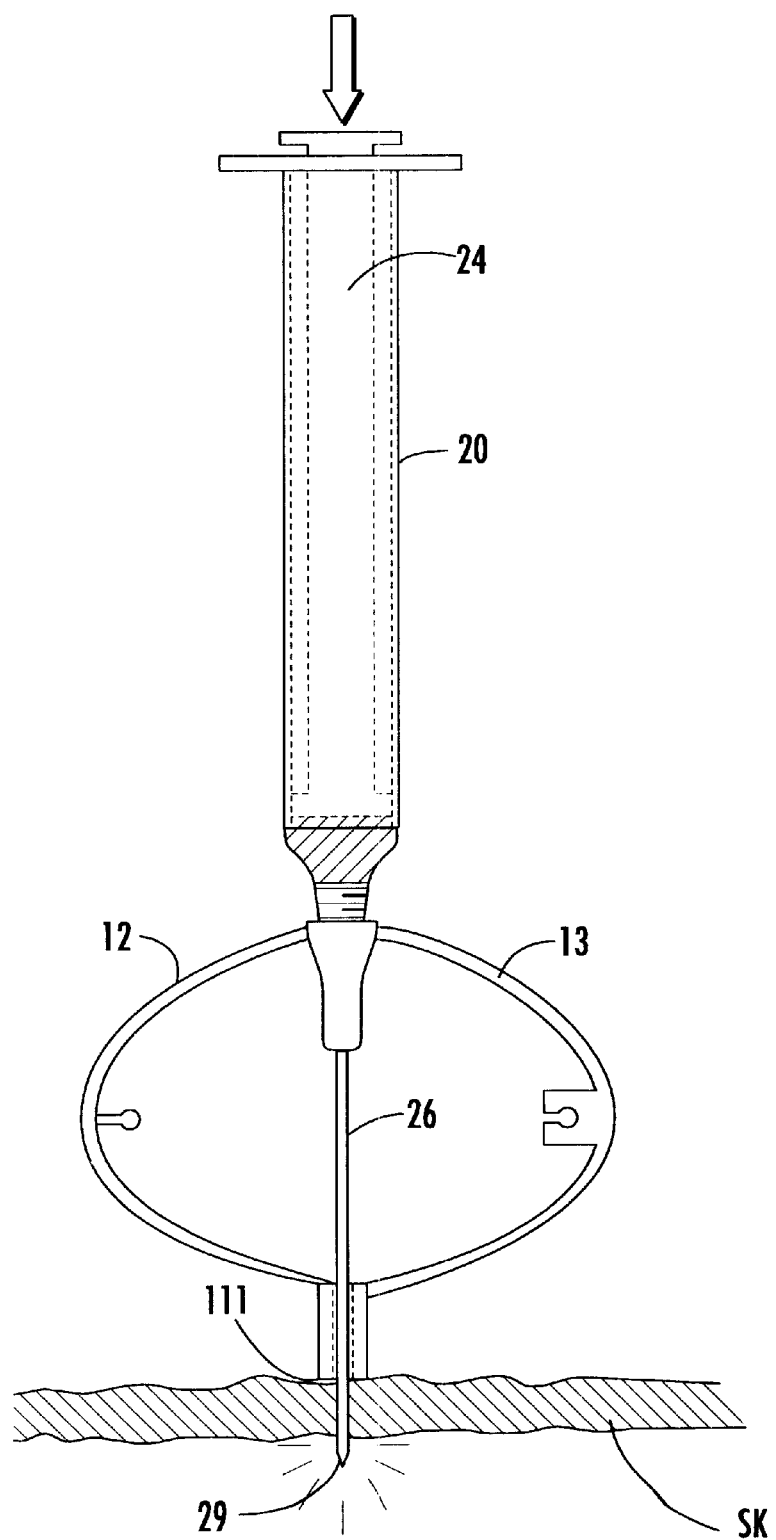
FIG. 2 is a side perspective view of a safety syringe delivering an injection.
Figure 3:
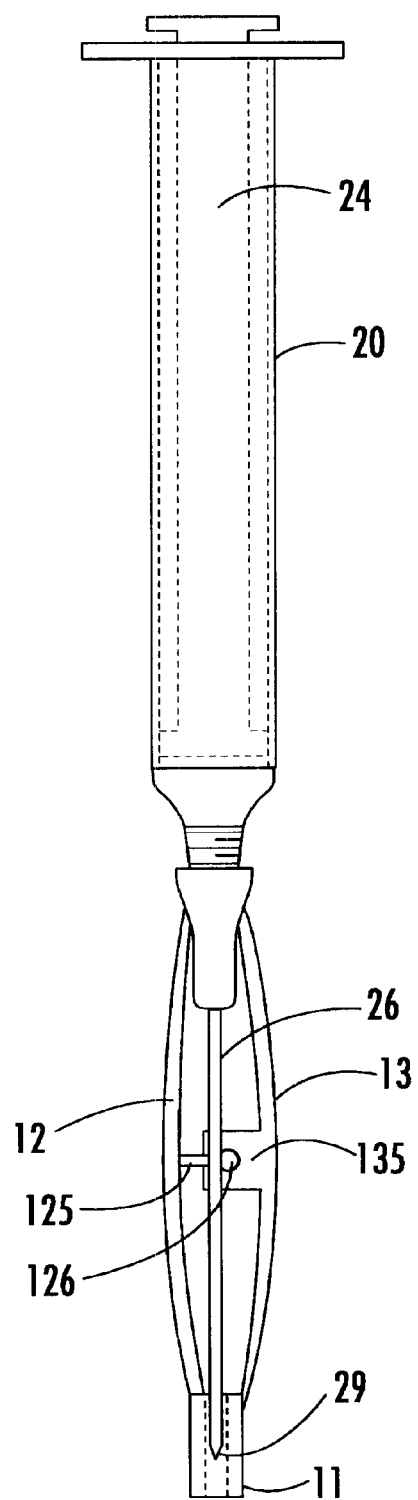
FIG. 3 is a side perspective view of a safety syringe following usage in the shielded and locked position.

A first embodiment of a safety mechanism 10, illustrated in FIGS. 1–3, comprises a sheath 11 having a longitudinal bore 110 extending from a distal end 111 to a proximal end 112. The bore 110 is adapted to slidingly admit a portion of the needle 26. The sheath 11 comprises a generally cylindrical, inflexible member that has sufficient strength to prevent penetration by the needle tip 29.

The safety mechanism 10 further comprises a pair of arms 12,13. Each of the arms 12,13 has a proximal end 121,131 that is affixed to the mating element 30 and a distal end 122,132 that is affixed adjacent the sheath's proximal end 112. The arms 12,13 are movable between a shielding position wherein the sheath 11 is in covering relation to the needle tip 29 (FIG. 1) and an injecting position wherein the needle tip 29 extends beyond the sheath's distal end 111 (FIG. 2).

In this embodiment the arms 12,13 each comprise a metal strip 123,133, the arms 12,13 positioned in generally opposed relation about the needle 26. Each metal strip 123,133 is outwardly bowed in the injecting position and is biased toward a more straightened orientation for moving toward the shielding position. In order to achieve shielding, the arms 12,13 are dimensioned so that the sheath 11 will cover the needle tip 29 when they are not under tension.

In a preferred embodiment, the arms 12,13 further comprise a flexible housing 124,134 that is affixed in covering relation to an outside face of the metal strip 123,133 (FIG. 1A). Each of the housings 124,134 in an exemplary embodiment comprises a plastic enclosure having a generally "C"-shaped axial cross section adapted to cover the outside face and edges of the metal strip 123,133.

The arms 12,13 are lockable in the shielding position, which feature will typically be invoked after the syringe 10 has been used to protect the needle tip 29 for disposal (FIG. 3). In this embodiment there are provided a pair of interlocking elements, one affixed on an inner face of each of the arms 12,13. The interlocking elements are adapted to engage when the arms 12,13 are in the shielding position. In a particular embodiment a first of the pair of interlocking elements comprises a post 125 affixed at a first end to a first 12 of the arms and a generally ball-shaped member 126 affixed to a second end of the post 125 opposed to the first end. A second of the pair of interlocking elements comprises a receptacle element 135 affixed to a second 13 of the arms and having a generally ball-shaped indentation 136 adapted to receive and restrain from removal the ball-shaped member 126.

Figure 4:
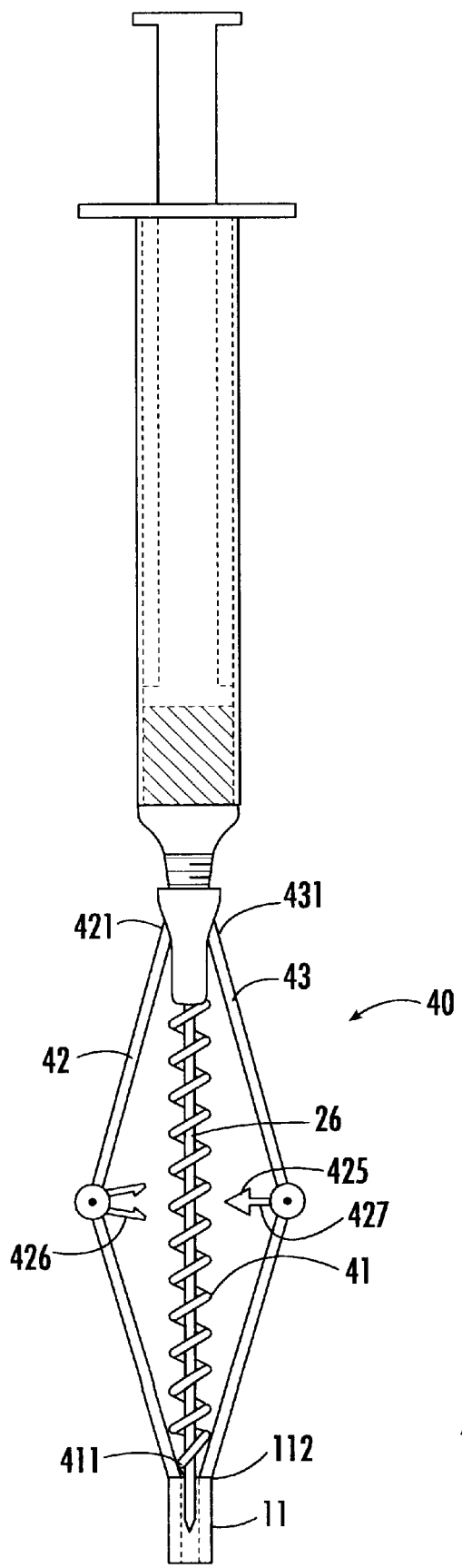
FIG. 4 is a side perspective view of an alternate embodiment of a safety syringe prior to usage.

In a second embodiment of the safety syringe, the safety mechanism 40, illustrated in FIG. 4, the arms 42,43 each comprise a hinged arm positioned in generally opposed relation about the needle 26. Each arm is outwardly bent in the injecting position and movable toward a more straightened orientation for moving toward the shielding position.

In this embodiment the biasing means comprises a coil spring 41 that has a generally central longitudinal space therethrough. The spring 41 is affixed to the sheath's proximal end 112 at a distal end 411 thereof and adjacent the proximal ends of the arms 421,431.

Interlocking elements 425,426 are also provided, affixed to the inward-facing sides of the arms 42,43. In this embodiment, a generally conically shaped protrusion 425 is affixed to a post 427, pointed end facing away from the arm 43, the post 427 affixed to arm 43. A mating element is affixed to the other arm 42 and comprises a receptacle 426 having an inner space adapted to interlock the protrusion 425 therewithin through a deformable entry passage.

The safety syringes 10,40 may be used as follows to inject a fluid substance into a patient: The needle's distal tip 29 is abutted against a site desired to be injected, such as skin SK, with the tip 29 shielded by the sheath 11 (FIG. 1). The syringe barrel 20 is moved toward the site, which causes the needle tip 29 to protrude distal of the sheath 11 and move the sheath 11 to the injecting position.

Next the external tissue at the site SK is penetrated with the needle tip 29 and the desired fluid is delivered (FIG. 2). Finally the needle tip 29 is removed from the site, and the tip 29 becomes covered by the sheath 11 as it moves and is locked into the shielding position (FIG. 3).

A second embodiment of a safety mechanism comprises a fluid sample collection implement 50. Such an implement 50 can be used, for example, to collect blood from a patient. The implement includes a housing 51 that has a proximal 52 and a distal 53 opening and an interior space 54. Communicating with the distal opening 53 is a tube-access needle (not shown).

A vacuum tube 55 is adapted to slide within the barrel's interior space 54 from the proximal end 56. The tube 55 is sealable within the housing 51, and has a distal opening 57 into an evacuated interior space 58 for holding a fluid sample. The vacuum tube 55, similar to those that are known in the art, comprises a sealing membrane across the distal opening 57 that is pierceable by the tube-access needle when fluid collection is desired to begin.

A fluid-collection needle 59 is affixed to the housing 51 at a distal end 591 thereof. The needle 59 has a bore 592 in communication with the housing's distal opening 53 and the tube's distal opening 57. The needle 59 also has a distal tip 60.

Figure 5:
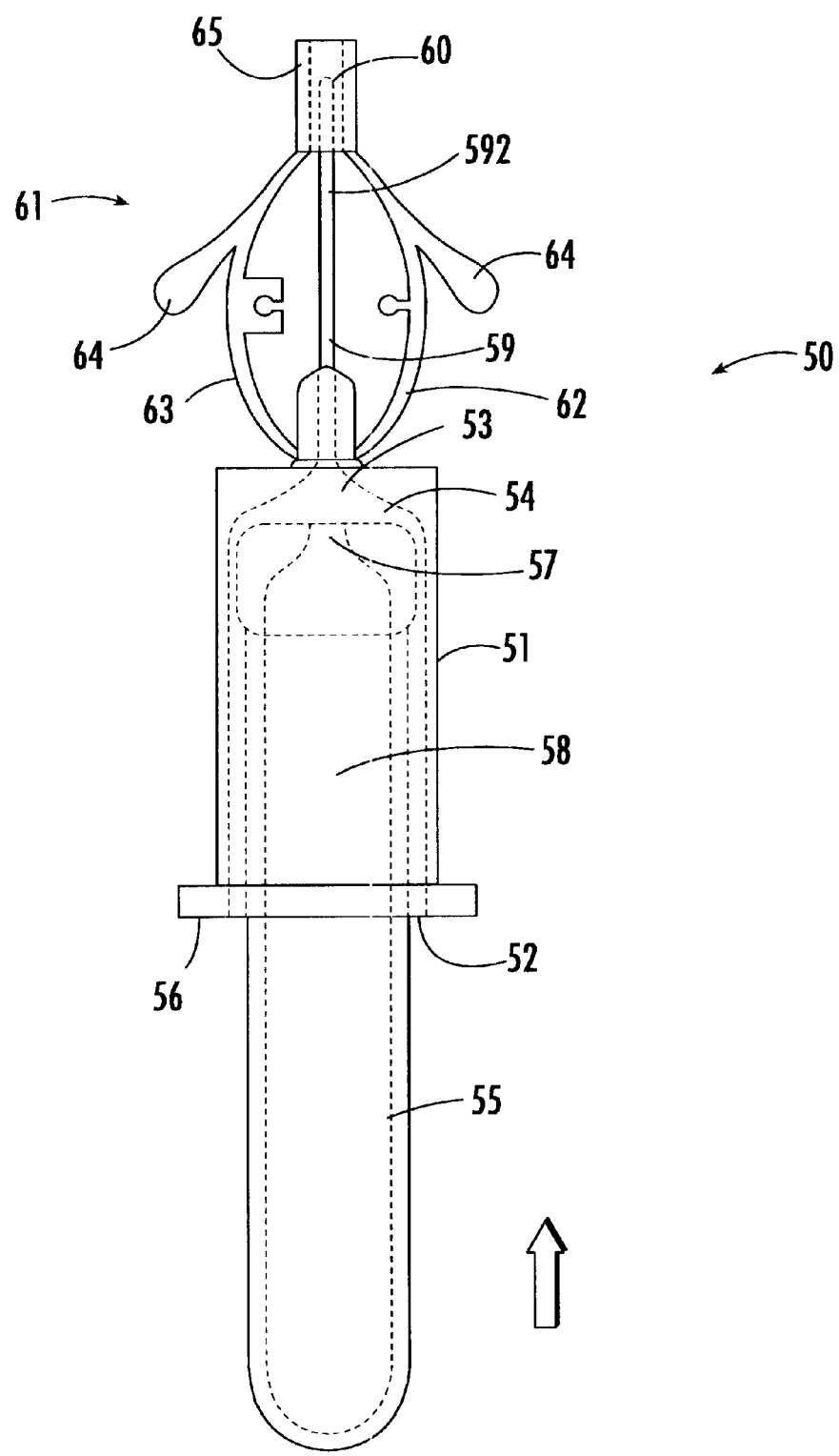
FIG. 5 is a side perspective view of a safety blood collection device.

A safety mechanism such as those 10,40 described above is affixable to the housing 51 and is used in an analogous way. In FIG. 5 is illustrated a safety mechanism 61 analogous to mechanism 10, although this is not intended as a limitation. An additional feature of this embodiment comprises an outwardly extending handle 64 affixed to the outside of each arm 62,63. The handles 64, which are shown as generally teardrop-shaped, are adapted to facilitate moving the arms 62,63 from the shielding position to the collection position.

In use the device 50 is employed to collect a fluid from a patient by abutting the needle's distal tip 60 against the site from which fluid is desired to be collected. At this point the tip 60 is covered by the safety sheath 65. Next the housing 51 and fluid collection tube 55 is pressed toward the site, and the sheath 65 is withdrawn into the collection position, wherein the needle tip 60 protrudes distal of the sheath 65.

External tissue at the site is then penetrated with the needle tip 60, and the desired fluid is withdrawn. Finally, the needle tip 60 is removed from the site, and the tip 60 is covered by the sheath 65 moving into and being lockable in the shielding position.

It may be appreciated by one skilled in the art that additional embodiments may be contemplated, including safety tips for other puncturing or surgical implements.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A safety syringe comprising:

a barrel having a proximal and a distal opening and an interior space;

a plunger adapted to slide within the barrel interior space from a proximal end;

a needle affixed to the barrel at a distal end having a bore in communication with the barrel distal opening and a distal tip; and a safety mechanism comprising:
  a sheath having a longitudinal bore extending from a distal end to a proximal end, the bore adapted to slidingly admit a portion of the needle;
  a pair of arms, each having a proximal end affixed adjacent the barrel distal end and a distal end affixed adjacent the sheath proximal end, the arms movable between a shielding position wherein the sheath is in covering relation to the needle tip and an injecting position wherein the needle tip extends beyond the sheath distal end, wherein the arms each comprise a metal strip and a flexible housing affixed in covering relation to an outside face of the metal strip, each metal strip is positioned in generally opposed relation about the needle and outwardly bowed in the injecting position and biased toward a more straightened orientation for moving toward the shielding position; and means for locking the arms in the shielding position.

2. The safety syringe recited in claim 1, wherein the housings each comprise a plastic enclosure having a generally "C"-shaped axial cross section adapted to cover the outside face and edges of the metal strip.

3. The safety syringe recited in claim 1, wherein the sheath comprises a generally cylindrical, inflexible member.

4. The safety syringe recited in claim 1, wherein the locking means comprises a pair of interlocking elements, one affixed on an inner face of each of the arms, the interlocking elements adapted to engage when the arms are in the shielding position.

5. The safety syringe recited in claim 6, wherein:
   a first of the pair of interlocking elements comprises a post affixed at a first end to a first of the arms and a generally ball-shaped member affixed to a second end of the post opposed to the first end; and
   a second of the pair of interlocking elements comprises a receptacle element affixed to a second of the arms and having a generally ball-shaped indentation adapted to receive and restrain from removal the ball-shaped member.

6. A safety mechanism for shielding a syringe needle tip comprising:
   a sheath having a longitudinal bore extending from a distal end to a proximal end, the bore adapted to slidingly admit at least a distal portion of a needle;
   a pair of arms, each having a proximal end adapted to be affixed adjacent a distal end of a syringe barrel and a distal end affixed adjacent the sheath proximal end, the arms movable between a shielding position wherein the sheath is in covering relation to a tip of the needle and an injecting position wherein the needle tip extends beyond the sheath distal end, wherein the arms each comprise a metal strip and a flexible housing affixed in covering relation to an outside face of the metal strip, each metal strip is positioned in generally opposed relation about the needle and outwardly bowed in the injecting position and biased toward a more straightened orientation for moving toward the shielding position; and means for locking the arms in the shielding position.

7. A method for making a safety shield for a needle tip comprising the steps of:
   affixing a distal end of each of a pair of flexible arms to a sheath in generally opposed relation to each other, the arms having an injecting position wherein the needle tip extends beyond the sheath and are biased to a generally straightened, shielding position, the sheath having a longitudinal bore extending from a distal end to a proximal end, the bore adapted to slidingly admit a portion of a needle, the arms each having one of an interlockable pair of members affixed to an interior side, the arms dimensioned to place the sheath in covering relation to a needle tip when in the shielding position and to permit locking together of the interlockable pair of members, wherein the arms each comprise a metal strip and a flexible housing affixed in covering relation to an outside face of the metal strip, each metal strip is positioned in generally opposed relation about the needle and outwardly bowed in the injecting position and biased toward a more straightened orientation for moving toward the shielding position; and
   affixing a proximal end of each arm to a mating element adapted to mate with a medical implement housing.

\* \* \* \* \*